United States Patent [19]

Watts

[11] 4,313,932

[45] Feb. 2, 1982

[54] DRY SOLIDS MIXED FOR HAIR BLEACHING COMPOSITIONS

[75] Inventor: Ronald E. Watts, Harlow, England

[73] Assignee: Minnesota Mining and Manufacturing Company, St. Paul, Minn.

[21] Appl. No.: 703,369

[22] Filed: Jul. 8, 1976

[30] Foreign Application Priority Data

Jul. 14, 1975 [GB] United Kingdom ............... 29489/75
Oct. 8, 1975 [GB] United Kingdom ............... 41298/75

[51] Int. Cl.$^3$ ............................................... A61K 7/135
[52] U.S. Cl. ......................................... 424/62; 8/111; 252/186; 424/DIG. 3
[58] Field of Search ................ 252/186; 424/DIG. 3, 424/62; 8/111; 132/7

[56] References Cited

U.S. PATENT DOCUMENTS

| | | | |
|---|---|---|---|
| 2,991,228 | 7/1961 | Lustig | 424/62 |
| 3,193,464 | 7/1965 | Edman et al. | 424/62 |
| 3,378,444 | 4/1968 | Swanson | 424/62 |
| 3,499,844 | 3/1970 | Kibbel et al. | 424/62 X |
| 3,726,967 | 4/1973 | Vorsatz | 424/62 |
| 3,816,615 | 6/1974 | Zeffren et al. | 424/62 |
| 3,997,659 | 12/1976 | Knohl et al. | 424/62 |

FOREIGN PATENT DOCUMENTS 859276 1/1961 United Kingdom ................ 424/62

OTHER PUBLICATIONS

Zimmerman et al., Industrial Research Service's Supplement II to the 1953 Edition of *Handbook of Material Trade Names* (1957), Industrial Research Service Inc., Dover, N.H., p. 40.

*Encyclopedia of Polymer Science and Technology*, vol. 1, John Wiley & Sons, Inc. (1964), pp. 177, 187–189, 192, 197, 209, 213, 214, 221 and 222.

*Primary Examiner*—Natalie Trousof
*Assistant Examiner*—Vera C. Clarke
*Attorney, Agent, or Firm*—Cruzan Alexander; Donald M. Sell; Mark A. Litman

[57] ABSTRACT

A composition which forms a hair bleaching solution when mixed with water comprising: hydrogen peroxide liberator, ammonia liberator, thickener and alkaline compound. A bleach accelerator and heavy metal complexing agent are preferably used in this composition.

1 Claim, No Drawings

DRY SOLIDS MIXED FOR HAIR BLEACHING COMPOSITIONS

This invention relates to hair bleaching compositions.

There are many hair bleaching compositions on sale both to the general public and to professional hairdressers. The compositions are of two main categories; the strong bleaching formulations which are intended to bleach dark hair to a very pale color and the mild bleaching formulations which are intended to lighten hair color only slightly.

The strong hair bleaching compositions are normally sold as a pack of at least two or often three containers whose contents are mixed immediately prior to use. One component of such strong hair bleaching compositions is usually a hydrogen peroxide solution. Such packs have a number of practical disadvantages. More than one container is required. There is usually a special order for mixing the components, e.g. solids must first be mixed with one of the liquids before the second liquid is added, otherwise the mixture of the two liquids is usually too viscous for the solids to be dispersed satisfactorily. Furthermore, when mixing small quantities from each container, errors in the relative proportions can easily occur.

It is therefore an object of this invention to provide a dry, solids composition which will give a strong bleaching composition upon mixing with water.

According to the invention there is provided a dry, solids power composition comprising:

(a) a hydrogen peroxide producer compound which will release or generate hydrogen peroxide when dissolved in water and which is a stable solid when dry, (b) an ammonium compound which will release or generate ammonium ions when dissolved in water, (c) a thickener which will readily disperse in alkaline solution, and (d) an alkaline compound which will give the composition an alkaline pH when it is dissolved in water, the alkaline compound being optionally constituted in part or in total by one or more of the previous components such as the hydrogen peroxide producer compound, (e) a bleach accelerator selected from alkali metal and ammonium peroxydisulfates and peroxydiphosphates (in certain compositions this component e may not be essential).

Such a powder composition is very simple to use since all the user has to do is mix it with the appropriate amount of water to provide a strong bleaching composition. Thus there is no problem of the correct order of mixing and only a single simple container is required. It is readily possible to prepare a small accurate sample for testing the bleaching time required. The dry powder composition can have good storage stability or shelf life. Furthermore, the composition can be sold in a simple, single, sealed packet or other container and the composition may be mixed by the user with water. Tap water may even be used.

The preferred compositions of the invention additionally contain a heavy metal complexing agent such as ethylenediaminetetraacetic acid or one of its salts, e.g. the sodium salt. This agent will complex any traces of heavy metal ions which may be present in the other components or in tap water, these metal ions otherwise being liable to catalyze both the decomposition of the bleaching composition (particularly the hydrogen peroxide producer with consequent loss of bleaching efficiency during use) and the formation of foam which can lead to irregular hair bleaching.

The hydrogen peroxide producer compound, component a, is a compound which will release the hydrogen peroxide required to perform the hair bleaching when the dry powder composition is dispersed with water. The compound must be stable when dry so as to ensure that the dry powder composition has a good shelf life. The compound can be a peroxide or a perhydrate, namely compound which has hydrogen peroxide in place of the water of crystallization in crystalline forms of a compound. Examples of hydrogen peroxide producer compounds are urea perhydrate, sodium phosphate perhydrate and citric acid perhydrate. The preferred compound is sodium carbonate perhydrate because it has excellent long term stability when dry and is readily available commercially.

As noted above, component d, the alkaline compound, can be one of the previous components a to c and e fulfilling the additional function of component d, giving the alkaline pH to the bleaching composition. When sodium carbonate perhydrate is used as component a, it will give the dry powder composition an alkaline pH when dispersed in water and so sodium carbonate perhydrate can constitute both component a and component d. When a separate component d is required, examples of suitable compounds for component d are potassium carbonate, sodium carbonate and sodium phosphate. Once the powder compositions of the invention have been dispersed or dissolved in water they must give a bleaching composition with an alkaline pH for the hydrogen peroxide release to be effective and so the choice of component d must be made with this in mind.

The bleach accelerator, component e, appears to act as a booster for the bleaching action of the hydrogen peroxide released when the powder composition is mixed with water. Other peroxydisulfates (all alkali metal and ammonium) will also give this boosting action but do not appear to be as desirable for use in the dry powder compositions of the invention. Thus potassium peroxydisulfate has a relatively low solubility in water and so could not readily be dissolved in water as required by the compositions of the present invention and ammonium peroxydisulfate is unstable in its solid form and so a dry composition which included it would not have a satisfactory shelf life. The art recognizes equivalency between peroxydiphosphates and the peroxydisulfates as accelerators. The latter are preferred, but the former are useful in the practice of this invention.

The ammonium compound, component b, should have good stability when dry and must readily dissolve in water. It should give ammonium ions in solution since it appears to be the case that better hydrogen peroxide hair bleaching is achieved in the presence of ammonium ions than in their absence. Examples of suitable ammonium compounds are ammonium carbonate, ammonium nitrate and ammonium chloride, while the presently preferred ammonium compound is ammonium sulphate.

The thickener, component c, must be one which will readily disperse in an alkaline solution. The function of the thickener is to give a bleaching composition which can be applied to the hair and will remain in contact with the hair and not run off during the bleaching period.

For best bleaching the degree of thickening or viscosity of the bleaching composition is relatively important since a composition which is too thick tends to give a poor or uneven bleach because it will not penetrate between the hairs and a composition which is too thin will drip off the head and cannot be retained to bleach localized regions. A simple test to check whether the viscosity is satisfactory is to test the bleaching of a test swatch of hair to see whether even bleaching occurs and whether the composition stays on the swatch without running off.

Because the compositions of the invention are sold in a dry powder form which is capable of being stored for a long time, one cannot easily use conventional purely organic thickeners, such as ammonium salts of long chain fatty acids, on their own since they cannot readily be dried and then redissolved. Other thickeners such as relatively large quantities of insoluble inorganic material can be used easily, e.g. calcium carbonate, magnesium carbonate, particularly light magnesium carbonate (magnesia alba levis), plaster of paris (calcium sulphate hemihydrate) talc, kaoline, magnesium trisilicate and bentonite, optionally together with a humectant such as sugar to prevent drying out. Further the thickener can be a gel forming compound of composition such as anhydrous, water dispersible, alkaline gel-forming silicate of an alkali metal such as sodium metasilicate.

The presently preferred thickening composition contains a finely divided silica which therefore has a large surface area and which will aggregate because of hydrogen bonding when dispersed in a liquid and so give a thixotropic effect. Preferably this silica is used together with additives which have a synergistic thickening effect with the silica and which are surfactants (preferably cationic), gelatin, homopolymers and copolymers of both acrylamides and acrylic polymers which will form a viscous solution in the presence of alkaline liquids. The presently preferred thickener is a mixture of the silica and the acrylic polymers.

The silica preferably has an average particle size of no more than 6μ, the practical lower limit of particle size being about 0.007μ, while the preferred particle size is about 0.01μ. Such materials can be made by the high temperature hydrolysis of silicon tetrachloride and a number of such materials are commercially available such as Cabosil from the Cabot Corporation. Other suitable silica particles are available under the trade name Santocel from Monsanto. It is believed that the silica particles should be in the form of spheroids with a relatively smooth surface and little or no internal porosity.

One preferred group of acrylic polymer latices have some hydrophillic groups such as carboxylic groups to make the polymers readily dispersible in water and esters or like groups which will hydrogen bond with the silica particles. These acrylic polymer latices are themselves thickeners of aqueous systems forming a milky latex with water of acid pH values and a clear gel with water of neutral or alkaline pH values. The acrylic polymer latex is desirably one which contains some free carboxyl groups. A group of useful latices are those which are sold by Rohm and Haas under the name Acrysol. An example of these materials which we have found effective is referred to by the makers as ASE-95 and is described by them as an acrylic emulsion copolymer. This readily dissolves or disperses to form a clear highly viscous system in an alkaline solution.

Because the thickener has to be in a dry powder form for incorporation into the compositions of the invention, we have found it to be advantageous for the finely divided silica and the aqueous acrylic polymer latex to be mixed and then the mixture dried and finely ground or spray dried to give fine particles. The resulting product is readily dispersible dependent upon the particle size of the thickener powder. Particle sizes which enable ready dispersion in water (that is, within 2 mins. with shaking and/or hand stirring) are desirable. Particle sizes of less than about 150μ are preferred. The dried latex without the silica is not easily ground or redispersed and, in addition, the drying of a mixture of the latex and silica has the advantage over a mixture of the separately dried latex and silica of binding the silica particles which are otherwise so fine that they can readily be blown about by air currents and may be able to stick to glass and plastic surfaces because of electrostatic charges.

The amount of residual water in the thickener powder appears to have some limited effect upon the properties of the thickener of the invention. We have found that good results are given when the dried mixture of silica and latex has a residual water content of about 2% by weight although both a larger or smaller residual water content in the dried mixture would be satisfactory. Significantly higher percentages will initiate the release of hydrogen peroxide from the component (a) and should be avoided and may also make the thickener sticky which is usually undesirable.

Of the mixture of silica and latex, the latter desirably forms on a dry basis from 14 to 40%, and preferably about 24%, by weight of the mixture of the two.

The silica has also been found to give very effective thickening when mixed with various cationic surfactants such as cetyltrimethylammonium bromide, dodecyltrimethylammonium bromide, hexadecylpyridinium bromide, the di-acetate salt of tallow diamine (e.g. Duomac T of Armour Chemicals), cocodiamine (e.g. Duomeen CD of Armour Chemicals), coco amine (e.g. Armeen C of Armour Chemicals), the acetate salt of coco amine (e.g. Armac C of Armour Chemicals) and tallow diamine (e.g. Duomeen T of Armour Chemicals), various betaine surfactants such as that sold by Glovers Chemicals under the name Ambiteric D, and polyfunctional compounds such as gelatin. In any case where these compounds are solutions, they can be dried and ground after mixing with the silica in a fashion analogous to that described for the acrylic polymer latices. When, on the other hand, they are solid, they can be ground finely, mixed with the silica and then this mixture added to the other components of the compositions of the invention.

Of mixtures of the silica and these surfactants or polyfunctional compounds, the surfactants or polyfunctional compounds desirably form on a dry basis from 10 to 24% by weight of the mixture.

Other additives for mixing with the silica to give a thickener for use as component c are homopolymers and copolymers of acrylamide. There are a wide range of these polymers which can range from cationic polymers through non-ionic polymers to anionic polymers. Such polymers can have high molecular weights. They can be made available as free flowing powders which will dissolve in water to give very viscous clear solutions. Accordingly they are excellent for incorporation together with the silica into the powder compositions of the invention. Examples of suitable acrylamide polymers are those sold by Cyanamid International under the trade name Cyanamer, e.g. A370, P26 and P250, and those sold by Cyanamid International as flocculants under the trade name Superfloc, e.g. Superfloc C100, Superfloc C110 (both cationic acrylamide homopolymers), Superfloc N100, Superfloc N100S (both neutral acrylamide homopolymers) and Superfloc A from A100 to A150 (all anionic acrylamide homopolymers), the higher the number the larger the anionic charge.

At the moment these acrylamide polymers are not preferred over the above described acrylic polymer latices for use with the finely divided silica as thickeners in the compositions of the invention because they appear to lose some of their thickening properties during storage. Compositions containing these acrylamide polymers, however, do appear to expand less during bleaching, give slightly better bleaching and, because they are available as dry powders and not aqueous latices, they do not need to be dried before incorporation into the polymer composition. However mixtures of the silica and acrylamide polymers retain the disadvantageous fluffy nature of the silica powder and so compositions containing silica and the acrylic polymer latices are more readily handleable.

Of the mixture of silica and acrylamide polyer the latter desirably forms on a dry basis from 0.5 to 8%, and preferably from 1 to 4%, by weight of the mixture of the two.

The relative proportions of the various components of the compositions of the invention are set by, amongst others, the desire to achieve a good bleach without harm to the hair or the user, the need to have regard to the toxicity and danger of the use on the human body of a composition which is too highly alkaline or a composition which contains too high a concentration of hydrogen peroxide producer, the need for bleaching to occur reasonably quickly at ambient temperatures and the composition of the thickener. Preferred and particularly preferred compositions according to the invention contain the following ranges by weight of components:

| | preferred | particularly preferred |
|---|---|---|
| (a) hydrogen peroxide producer compound | 13 to 43% | 30 to 36% |
| (b) ammonium compound | 1.4 to 12.5% | 5 to 8% |
| (c) thickener | 14 to 32% | — |
| (d) alkaline compound | this is preferably the hydrogen peroxide producer compound | |
| (e) alkali metal or ammonium peroxydisulfate or peroxydisphosphate | 13 to 43% | 30 to 36% |
| (f) complexing agent (if present) | 1.4 to 12.5% | 5 to 8%. |

Two preferred compositions by weight according to the invention are as follows:

| | | |
|---|---|---|
| sodium carbonate perhydrate | 33.3% | 34.0% |
| ammonium sulphate | 6.7% | 6.8% |
| thickener (mixture of an Acrysol and Cabosil) | 20.0% | — |
| thickener (mixture of an acrylamide homopolymer and Cabosil) | — | 18.0% |
| sodium peroxydisulfate | 33.3% | 34.0% |
| EDTA sodium salt | 6.7% | 6.8%. |

The dry powder compositions of the invention are desirably in a finely ground form with a particle size of less than 1 mm and so they can be readily dissolved or dispersed in the required amount of water. Certain components of the mixture, such as the thickener are, however, more difficult to disperse or dissolve that the other components of the invention and so it is preferred for those more difficult components to have a much smaller particle size. For use they are merely mixed with water. Hydrogen peroxide is not required. The compositions are mixed with water in an amount such as from 20 to 40 parts by weight of dry powder composition per 100 parts by weight of the mixture of water and dry powder composition. The correct amount of water can be indicated to the user by providing the powder composition in a flexible packet, e.g. a plastics bag or sachet, of such a size that when the contents are dispensed into a container, the right amount of water can be added to fill the packet and then also added to the container.

The resulting bleaching composition is a strong bleach without the addition of hydrogen peroxide and will bleach dark hair completely. It is found that compositions of the invention will give well bleached hair without excessive yellow or red residual coloration. Therefore it is usually unnecessary for the compositions of the invention to include a "drabber", i.e. a blue dye of pigment, to act as a toner to mask such yellow or red residual colorations. The bleaching compositions also have a relatively low ammonia odor and so it is usually not necessary for the compositions of the invention to include a perfume although the incorporation of a perfume may sometimes be desirable. The compositions of the invention can include other conventional hair bleaching constituents such as surfactants and conditioners but they are not usually necessary.

The invention will now be illustrated by the following examples.

EXAMPLE 1

To prepare the thickener, 2 ml of Acrysol ASE 95 (a copolymer of 40% methacrylic acid and 30%/30% comonomers of lower alkyl acrylates and methacrylates selected from (1) ethyl and methyl acrylate and (2) methyl and ethyl methacrylate. The polymer dissolves or disperses in alkaline aqueous solution) was diluted with 6 ml of water and then stirred into 1.25 g of silica (Cab-O-Sil MS-7) to form a smooth cream. This was then dried to remove the water leaving a coarse granular material which was ground to pass a sieve with 150 $\mu M$ apertures.

The following mixture was then prepared, the mixture having particles of a size less than 1 mm:

2.5 g sodium carbonate perhydrate,
2.5 g sodium peroxydisulfate,
0.5 g ammonium sulphate,
0.5 g ethylenediaminetetraacetic acid disodium salt,
and 1.5 g thickener prepared as above.

This mixture was placed in a beaker and 17 ml of water were added which was stirred in to produce the bleach. The pH was measured and found to be 9.4.

A 1.0 g swatch of dark brown hair was then placed into the beaker and the bleach worked into it. The hair was then removed from the beaker and held vertically and it was observed that the thick coating of bleach mixture showed no tendency to drip. The hair was then returned to the beaker which was placed in a thermostat bath at 35° C. for one hour. At the end of this time the pH was again measured and found to be unchanged. No surface drying of the bleach mixture was observed. The mixture was rapidly and easily removed from the hair by washing in running water and the hair was found to be uniformly bleached to a pale straw color. The bleached hair felt smooth and no surface roughening was visible under a microscope.

EXAMPLE 2

A batch of the dry powder mixture prepared as in Example 1 was placed in a moisture proof bag consisting of a polythene/aluminium/paper laminate and the free space flattened to remove air before heat sealing. The bag was then placed in an oven at 40° C. and lasted 40 days before the onset of gas evolution (evidence of reaction between the components) was just detectable. From a number of experiments this is believed to correspond to about 4 years keeping at 21° C.

EXAMPLE 3

To prepare a thickener, 0.05 g of Superfloc C110 (an acrylamide homopolymer in which some of the amide groups are converted to cationic groups. It has a molecular weight of several hundred thousand, and swells in alkaline aqueous solutions) were blended with 1.25 g of silica (Cab-O-Sil MS-7).

The following mixture was then prepared, the mixture having particles of a size less than 1 mm:

2.5 g sodium carbonate perhydrate,
2.5 g sodium peroxydisulfate,
0.5 g ammonium sulphate,
0.5 g ethylenediaminetetraacetic acid disodium salt,
and 1.3 g thickener prepared as above.

This mixture was placed in a beaker and 17 ml of water were added and stirred in to produce the bleach. The pH was measured and found to be 9.4.

A 1.0 g swatch of dark brown hair was then placed into the beaker and the bleach worked into it. The hair was then removed from the beaker and held vertically and it was observed that the thick coating of bleach mixture showed no tendency to drip. The hair was then returned to the beaker which was placed in a thermostat bath at 35° C. for one hour. At the end of this time the pH was again measured and found to be unchanged. No surface drying of the bleach mixture was observed. The mixture was rapidly and easily removed from the hair by washing in running water and the hair was found to be uniformly bleached to a pale straw color. The bleached hair felt smooth and no surface roughening was visible under a microscope.

EXAMPLE 4

A batch of dry powder mixture prepared as in Example 3 was placed in a moisture proof bag consisting of a polythene/aluminium/paper laminate and the free space flattened to remove air before heat sealing. The bag was then placed in an oven at 40° C. and lasted 40 days before the onset of gas evolution (evidence of reaction between the components) was just detectable. From a number of experiments this is believed to correspond to about 4 years keeping at 21° C.

What is claimed is:

1. A dry, solids powder composition for mixing with water to give a hair bleaching composition comprising:
   (a) a hydrogen peroxide producer compound comprising 13 to 43% by weight of said powder composition which produces hydrogen peroxide when dissolved in water and which is a stable solid when dry,
   (b) an ammonium compound comprising 1.4 to 12.5% by weight of said powder composition which will produce ammonium ions when dissolved in water,
   (c) a thickener comprising 14 to 32% by weight of said powder composition which readily disperses in alkaline solution,
   (d) an alkaline compound which will give the composition an alkaline pH when it is dissolved in water, the alkaline compound being optionally constituted in part or in total by one or more of the previous components, and
   (e) bleach accelerator comprising 13 to 43% by weight of said powder composition selected from the group consisting of (1) alkali metal and ammonium peroxydisulfates and (2) alkali metal and ammonium peroxydiphosphates, wherein said ammonium compound is ammonium sulfate and in which the thickener is finely divided silica and a synergistic additive selected from the group consisting of (1) a dried acrylic polymer latex which is capable of readily dissolving or dispersing in an aqueous alkaline solution to form a viscous system and (2) a homo- or copolymer of acrylamide which is capable of dissolving in water to give viscous solutions.

* * * * *